United States Patent [19]

Walters et al.

[11] 4,426,880

[45] Jan. 24, 1984

[54] METHOD AND APPARATUS FOR FLUID SAMPLING AND TESTING

[75] Inventors: John P. Walters; Radomir Petrovich, both of Bartlesville, Okla.; Gregory C. Daley, Dallas, Tex.; Donald C. Harban, Salt Lake City, Utah

[73] Assignee: Phillips Petroleum Company, Bartlesville, Okla.

[21] Appl. No.: 286,310

[22] Filed: Jul. 24, 1981

[51] Int. Cl.$^3$ .............................................. G01N 17/00
[52] U.S. Cl. ................................ 73/61.2; 73/863.21; 73/863.43
[58] Field of Search ............. 73/61.2, 53, 863.03, 73/863.43, 863.21; 374/7; 60/641.5, 641.2, 641.3, 641.4; 138/44; 436/6, 25, 28, 2

[56] References Cited

U.S. PATENT DOCUMENTS

| | | | |
|---|---|---|---|
| 2,363,625 | 11/1944 | Swearingen | 73/863.43 |
| 2,447,595 | 8/1948 | Pigott et al. | 73/863.43 |
| 2,752,077 | 6/1956 | Lung | 138/44 X |
| 2,790,463 | 4/1957 | Delano et al. | 138/44 |
| 3,141,324 | 7/1964 | Boies et al. | 73/61.2 |
| 3,552,189 | 1/1971 | Courvoisier et al. | 73/61.2 |
| 3,638,498 | 2/1972 | Nelms | 73/863.21 |
| 3,724,502 | 4/1973 | Hayner et al. | 138/44 |
| 3,913,378 | 10/1975 | Hausler | 73/61.2 X |
| 4,054,175 | 10/1977 | Swearingen | 60/641.2 X |
| 4,091,675 | 5/1978 | Jennison | 73/863.03 |
| 4,092,122 | 5/1978 | Suga | 23/253 C |
| 4,174,734 | 11/1979 | Bradham | 138/44 X |
| 4,176,544 | 12/1979 | Eyles et al. | 73/61.2 |
| 4,346,587 | 8/1982 | Brindak | 73/61.2 |

Primary Examiner—S. Clement Swisher
Assistant Examiner—John E. Chapman, Jr.

[57] ABSTRACT

An apparatus for preparing and testing fluid samples in which a two-phase fluid mixture passes through equipment for homogenizing the mixture with at least one isokinetic sampling device arranged to remove portions of the homogenized fluid mixture, with the portions then being passed through testing equipment. Preferably, geothermal fluid is homogenized and samples are withdrawn by the isokinetic sampling device and tested for various properties of the fluid, particularly the formation of scale. The testing apparatus is adapted for on-site operation.

10 Claims, 1 Drawing Figure

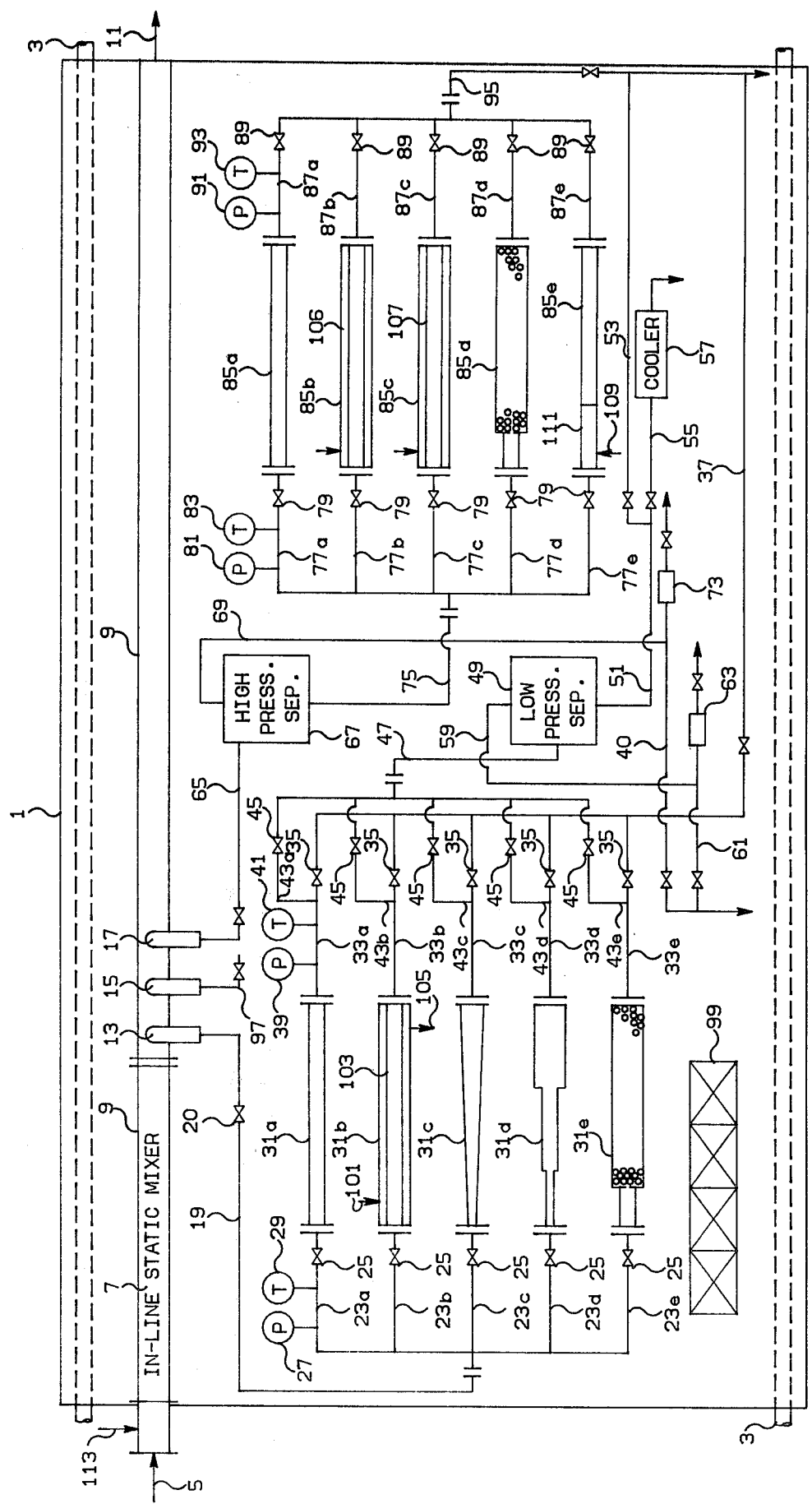

METHOD AND APPARATUS FOR FLUID SAMPLING AND TESTING

BACKGROUND OF THE INVENTION

This invention relates to the preparation and testing of fluid samples. In one of its aspects it particularly relates to the testing of two-phase fluid mixtures such as those found in geothermal fluid. In another aspect this invention relates to the testing of scaling properties of geothermal fluids. In yet another of its aspects this invention relates to on-site, portable test apparatus.

Reduced supplies and limited international exchange of energy resources have encouraged exploitation of all available energy sources. A major source of natural energy lies in the heated fluids that are found in geothermal basins. The exploitation of geothermal energy has, therefore, become important. A major problem with the exploitation of geothermal energy is caused by the fact that the geothermal liquid (brine) that carries the stored energy is highly corrosive and deposits scale in the equipment used in the utilization of the energy. Flow rates of 50,000 to 100,000 barrels of brine per day at temperatures of 100° to 340° C. can provide considerable useful energy; however, such flow rates containing from 5,000 to 250,000 ppm salt also provide a high rate of equipment deterioration which hinders the economical development of this source of energy.

It has become necessary to evaluate geothermal fluids to determine their scaling and corrosion potentials prior to economic investment. Until recently, however, most methods of evaluating scaling involved sampling well fluid and simulating well conditions away from the well site. Only limited evaluation of scaling and corrosion has been made using actual well fluids with the majority of data for scale evaluation being calculated from well parameters, i.e. flow rate, temperature, pressure, salinity, and the like.

The present invention is an on-site geothermal well test facility that is portable that is made up of an orifice meter, an isokinetic sampling nozzle, a non-condensable gas sample separator, and its own power station. This unit is utilized for determination of well characteristics, mass flow, pressure, temperature, enthalpy, and the like, using actual well fluid at the site of the well. Also the present invention is designed to provide an on-site, portable test apparatus for use in evaluating geothermal well parameters and developmental characteristics particularly aimed at determining corrosion and scaling characteristics. It can be seen that such a device would also be useful in testing fluid samples from any source that contains dissolved chemical compounds that can produce scaling and corrosion problems in production equipment.

It is therefore an object of this invention to provide an apparatus and method for obtaining and testing fluid samples. It is another object of this invention to provide apparatus and method for determining scaling and corrosion characteristics of geothermal liquid. It is still another object of this invention to provide specific apparatus and test methods for characterizing scaling from geothermal fluids. It is yet another object of this invention to test scale inhibitors.

Other aspects, objects and the various advantages of this invention will become apparent upon the study of this specification, the appended drawing, and the claims.

STATEMENT OF THE INVENTION

According to this invention an apparatus and method are provided for preparing and testing fluid samples to which a two-phase fluid is passed through a means for producing a homogenized mixture, portions of the fluid mixture discharged from the homogenizing means are removed by at least one means for isokinetic sampling and the portions of the fluid removed from the homogenized mixture are passed through means for testing characteristics of the fluid. In the preferred embodiment of the invention the fluid is a geothermal liquid mixed with steam and non-condensable gases and the means for testing comprises brine testing apparatus.

Although, as stated above, this invention can be useful in testing any type of two-phase fluid mixture, i.e., liquid containing non-condensable gases and/or steam which has the potential for releasing scale producing chemcials that have been held in solution, it is of particular interest in the preparation and testing of saline solutions. It has been designed for use on-site for the testing of geothermal mixtures produced from geothermal wells. The invention will, therefore, be described in conjunction with the drawing which is a schematic illustration of an apparatus useful according to the method of this invention.

Referring now to the drawing, the apparatus of this invention is installed upon a base structure 1 which is a rectangular framework or floor that provides a platform upon which the equipment is secured for transportation from place to place. The structure 1 is supported by pipe skids 3 or other sled-like runners to provide sliding mobility across rough terrain which is often encountered at the site of geothermal wells.

In the operation of the invention a two-phase fluid mixture which has as its usual components a geothermal liquid (brine), and the steam (which contains non-condensable gases) is passed from a geothermal well through line 5 into the static mixer 7 located in the transfer line 9 which traverses the portable structure 1 and is passed on through line 11 through geothermal production equipment or to be discharged back to the reinjection location or a waste pit.

The in-line static mixer 7 can be chosen from any of a number of commercially available apparatuses that will homogenize a two-phase geothermal fluid to the extent that the fluid diverted through the transfer line 9 of the portable device is equivalent in bulk chemical composition to the geothermal fluid emerging from the well and passing through the main transfer line through production equipment. For this purpose a Kenics Static mixer sized for transfer line 9 is preferred in carrying out the mixing function well.

As the homogenized two-phase fluid mixture is passed through line 9 portions of the mixture are removed through isokinetic sampling means 13,15,17 to be passed to means for testing these portions of the fluid. As illustrated, the isokinetic sampling devices, which are well known in the art are used in combination with the static mixer in instances in which truly representative samples that consist of two-phase fluid mixtures are being sampled, and are preferably placed as close to the outlet of the static mixer as possible.

The portion withdrawn through isokinetic sampler 13 is passed through line 19 which contains shut-off valve 20 into a manifold of pipes 23a-e each of which contains an individual shut-off valve 25 and each of which can be equipped with individual means for registering pressure and temperature 27,29 (here illustrated only in line 23a). Portions of the sample are passed through individual testing devices 31a-e and through an exit manifold 33a-e with each line containing a pressure regulating valve 35 with all of the flows joining together in line 37 to be discharged from the apparatus.

In each of the manifold lines 33a-e can also be located pressure and temperature indicating devices 39,41 (herein illustrated only on line 33a). To each of the manifold lines 33a-e corresponds a line 43a-e of an outlet transfer manifold. Each transfer line 43a-e contains a shut-off valve 45. Flows from the manifold transfer lines 43a-e pass through line 47 into low pressure separator 49. In the low pressure separator the liquid phase of the sample portions is separated and passed through line 51 and valved line 53 directly to discharge from the system or through valved line 55 and cooler 57 for sampling of the brine. The gaseous phase is removed from the separator 49 through line 59 to be discharged through valved line 61 or to be condensed in cooler 63 for measurement of the condensate and, by the addition of a rotameter system, measurement of the flow of non-condensable gases.

Similarly a portion of the homogenized two-phase fluid can be passed through isokinetic sampling means 17 and valved line 65 into a high pressure separator 67 in which the gaseous phase is separated from the liquid phase of the sample portion. The gaseous phase is passed through line 69 and valved line 40 directly to discharge from the system or through cooler 73 for collection of condensate and measurement of flow.

The liquid separated in the high pressure separator 67 is passed through line 75 into manifold 77a-e. This is similar to manifold 23a-e described previously with each of the manifold lines having a valve 79 and with the lines equipped with pressure and temperature indicating devices 81,83 (here illustrated only on lines 77a). The liquid flow is split into portions that are passed through testing devices 85a-e and through exit manifold 87a-e with each line equipped with a shut-off valve 89 and pressure and temperature indicating devices 91,93 (here illustrated only on line 87a). The liquid flows are reunited in valved line 95 to be discharged from the system.

Also illustrated is an isokinetic sampling device 15 which is used to draw a sample through line 97 into a variety of sampling containers so that the sample portions can be transferred to other points for chemical analysis from samples all of which can be tied directly into chemical analysis equipment at the site.

Since the apparatus of this invention is meant to be self contained the power pack or generating units here illustrated as 99 are also included on the structure 1 for easy transportation from place to place.

Some of the apparatus and methods for testing scaling produced by geothermal fluid that are contemplated for use according to this invention will be discussed below in testing procedure for the test units 31a-e and 85a-e. In actual practice these test units would be made up of flanged pipe six feet long that can be inserted into a test position with ease. Each of the testing procedures is designed to simulate an aspect of the handling of geothermal fluid to determine the effect of this handling on deposition of scale.

The fluid samples passing through test devices 31a-e are two-phase fluids which contain the liquid phase (brine) and the steam phase which includes non-condensable gases. The samples passing through test devices 85a-e have the vapor phase of the sample removed so that only the liquid phase (brine) is the tested fluid. In all of these tests it is the deposition of scale, i.e., the precipitation and attachment of solid phases from the liquid in the test devices either on the walls of the tubes or on the other solid surfaces within the tubes, that is the subject of the testing.

In all cases discussed below the inlet fluid samples are at temperatures in the range of about 200° to about 600° F. and a pressure in the range of about 150 to about 550 psig. The fluids will leave the test device at temperatures ranging from about 40° F. to about 600° F. and at pressures ranging from about 15 to about 550 psig. The test sections are designed for flow rates of up to about 10 liters per minute.

Referring now to test section 31a, which is a pipe of constant cross-section through which flow is passed as a reference, the deposition of scale on the walls of this tube indicate scaling that occurs because of decompression and/or cooling that has occurred upstream from the test section and provides data which are a basis for comparison with the other tests.

Referring now to test apparatus 31b, this test is a pipe of constant cross-section, preferably of the same size as 31a but also jacketed so that cooling fluid can be passed through inlet line 101, the jacket 103 and outlet line 105 to provide cooling down to a temperature as low as about 80° F. with a flow of about 10 liters per minute through the pipe.

Referring now to test apparatus 31c, which is a conical pipe with a larger diameter at the downstream end, passage of fluid through this pipe simulates progressive flashing in a well as the fluid is brought toward the surface.

Referring now to test apparatus 31d, which is a pipe that has abrupt increases in the cross-section so that the pipe becomes progressively larger toward the downstream end, passage of fluid through this pipe simulates scaling in separators, valves and similar apparatuses in which there is an abrupt change in cross-section.

Referring now to test apparatus 31e, which is a pipe of enlarged diameter which is filled with rock fragments approximating the mineralogy of the rock in the reservoir from which the geothermal fluid has been removed, passage of the fluid through this apparatus simulates the effect of rock substrate and irregular geometry on scaling caused by flashing in the reservoir itself.

The test apparatuses for the liquid phase from which the gaseous phase of the geothermal fluid has been removed are similar. The test apparatus 85a is identical to test apparatus 31a and test apparatuses 85b and 85c are identical to test apparatus 31b. In the simulation there may be interest in heating the liquid phase that has been cooled so that in test apparatus 85b,c of the fluid that is passed through jackets 106,107 can be either cooler than the liquid phase with the object of cooling the liquid phase to a temperature in the region of about 80° F. or can be hotter than the liquid phase with the object of heating the liquid phase to a temperature up to about 600° F., in both cases with a flow of about 10 liters per minute through the apparatus.

Similarly test apparatus 85d approximates the apparatus and method of testing the described above for 31e and is designed to study reactions between the liquid phase and the rocks in case reinjection of the brine into a reservoir is contemplated.

Referring to apparatus 85e which is a pipe of constant cross-section with a means for injecting aqueous solutions 109 and an inline mixer 111 situated at the upstream end of the device, a simulation can be carried out that studies scaling due to mixing of an aqueous solution with the liquid phase to determine its effect on precipitation of scale.

All of the test methods set out above can be used to determine the scale deposition characteristics of geothermal liquid as it is taken from the subterranean structure or by the addition of known amounts of chemical additives to the liquid before it enters the sampling stations 13,15,17, the effect of the additives on scale deposition can be determined. Provision for addition of chemical compounds such as inhibitors to the system is made at line 113 so that the additives are homogeneously mixed with the two-phase fluid system.

Other variations of test apparatus within the scope of this invention, such as providing heat exchange jackets for the apparatuses, described as 31c,31d,31e,85d, and 85e should be apparent to one skilled in the art.

It can be seen that the apparatus and methods described above are suitable for determining deposition of scale at geothermal well sites and are easily adaptable for determination of scaling in other situations.

We claim:

1. An apparatus for preparing and testing geothermal fluid samples comprising:
   (a) means for homogenizing a two-phase fluid mixture of geothermal liquid, steam and non-condensable gases,
   (b) at least one means for isokinetic sampling arranged to remove portions of the fluid discharged from said homogenizing means, and
   (c) means for monitoring scaling caused by said two-phase fluid mixture consisting of measurement of scale deposited by the removed portions passing through a constantly enlarging section of conical pipe.

2. An apparatus for preparing and testing geothermal fluid samples comprising:
   (a) means for homogenizing a two-phase fluid mixture of geothermal liquid, stream and non-condensable gases,
   (b) at least one means for isokinetic sampling arranged to remove portions of the fluid discharged from said homogenizing means, and
   (c) means for monitoring scaling caused by said two-phase fluid mixture consisting of measurement of scale deposited by the removed portions passing through a pipe of cross-section that increases in abrupt steps.

3. An apparatus of claim 1 or 2 wherein said apparatus is mounted on platform provided with skids.

4. An apparatus of claim 3 wherein power units for operation of components of the apparatus are mounted on this platform.

5. A method for preparing and testing geothermal fluid samples comprising in an apparatus of claim 1:
   (a) passing a two-phase fluid mixture of geothermal liquid, steam and non-condensable gases through said means for homogenizing to produce a homogenized two-phase fluid mixture,
   (b) isokinetically separating portions of said homogenized mixture, and
   (c) testing the separated portions to monitor scaling caused by said fluid mixture by measuring the scale deposited by the separated portions passing through a constantly enlarging section of conical pipe.

6. A method for preparing and testing geothermal fluid samples comprising in an apparatus of claim 2:
   (a) passing a two-phase fluid mixture of geothermal liquid, steam and non-condensable gases through said means for homogenizing to produce a homogenized two-phase fluid mixture,
   (b) isokinetically separating portions of said homogenized mixture, and
   (c) testing the separated portions to monitor scaling caused by said fluid mixture by measuring the scale deposited by the separated portions passing through a pipe of cross-section that increases in abrupt steps.

7. An apparatus for preparing and testing geothermal fluid samples comprising:
   (a) means for homogenizing a two-phase fluid mixture of geothermal liquid, steam and non-condensable gases,
   (b) at least one means for isokinetic sampling arranged to remove portions of the fluid discharged from said homogenizing means,
   (c) means for separating the liquid phase from the vapor phase of the removed portions of fluid thereby to monitor scale deposited in the separated liquid phase, and
   (d) means for monitoring scaling caused by said liquid phase consisting of measurement of scale deposited by said separated liquid phase passing through a pipe filled with rocks.

8. An apparatus of claim 7 wherein said apparatus is mounted on a platform provided with skids.

9. An apparatus of claim 8 wherein power units for operation of components of the apparatus are mounted on said platform.

10. A method for preparing and testing geothermal fluid samples comprising in an apparatus of claim 7:
    (a) passing a two-phase fluid mixture of geothermal liquid, steam, and non-condensable gases through a means for homogenizing to produce a homogenized two-phase fluid mixture,
    (b) isokinetically separating portions of said homogenized mixture,
    (c) separating the liquid phase from the vapor phase of the isokinetically separated portions, and
    (d) testing the separated liquid phase to monitor scaling caused by said liquid phase by measuring the scale deposited by said separated liquid phase passing through a pipe filled with rocks.

* * * * *